United States Patent
Juzbasic

(10) Patent No.: US 12,004,914 B2
(45) Date of Patent: Jun. 11, 2024

(54) CUSTOMIZED THREE-DIMENSIONAL SCAFFOLD FOR ORAL AND MAXILLOFACIAL BONE GRAFTING

(71) Applicant: DIP, LLC, Bethesda, MD (US)

(72) Inventor: Amir Juzbasic, Bethesda, MD (US)

(73) Assignee: DIP, LLC, Bethesda, MD (US)

( * ) Notice: Subject to any disclaimer, the term of this patent is extended or adjusted under 35 U.S.C. 154(b) by 513 days.

(21) Appl. No.: 17/470,286

(22) Filed: Sep. 9, 2021

(65) Prior Publication Data

US 2023/0074737 A1 Mar. 9, 2023

(51) Int. Cl.
| | |
|---|---|
| *A61C 13/00* | (2006.01) |
| *A61C 9/00* | (2006.01) |
| *A61F 2/30* | (2006.01) |
| *A61L 27/04* | (2006.01) |
| *A61L 27/58* | (2006.01) |

(52) U.S. Cl.
CPC ........ *A61C 13/0019* (2013.01); *A61C 9/0053* (2013.01); *A61C 13/0004* (2013.01); *A61L 27/047* (2013.01); *A61L 27/58* (2013.01); *A61F 2002/30948* (2013.01); *A61L 2430/12* (2013.01)

(58) Field of Classification Search
CPC .... A61L 27/047; A61L 27/58; A61L 2430/12; A61F 2002/30948; A61F 2002/30062; A61F 2002/30952; A61F 2002/30985; A61F 2/30942; A61F 2002/2889; A61F 2/2846; G16H 20/40; G16H 30/40; G16H 50/50; A61C 8/0006
See application file for complete search history.

(56) References Cited

U.S. PATENT DOCUMENTS

| | | |
|---|---|---|
| 9,211,362 B2 | 12/2015 | Hwang et al. |
| 10,136,969 B2 | 11/2018 | Juzbasic et al. |
| 10,300,171 B2 | 5/2019 | Stiefel et al. |

(Continued)

FOREIGN PATENT DOCUMENTS

| | | | |
|---|---|---|---|
| WO | 2010023665 A2 | 3/2010 | |
| WO | WO-2010023665 A2 * | 3/2010 | ............. A61C 1/084 |
| WO | 2017173333 A2 | 10/2017 | |

OTHER PUBLICATIONS

International Search Report and Written Opinion mailed Jan. 3, 2023 in related/corresponding International Application No. PCT/US22/42430.

*Primary Examiner* — Akwasi M Sarpong
*Assistant Examiner* — Michael L Burleson
(74) *Attorney, Agent, or Firm* — PATENT PORTFOLIO BUILDERS PLLC

(57) ABSTRACT

A customized resorbable three-dimensional scaffold for oral and maxillofacial bone grafting involves merging two sets of three-dimensional information obtained from a patient, the first set includes three-dimensional bone information and the second set includes three-dimensional teeth and tissue information. The merged information is used to generate a three-dimensional shape of the bone to be regenerated, a three-dimensional position of the missing tooth/teeth, and a three-dimensional model of the customized resorbable three-dimensional scaffold for oral and maxillofacial bone grafting. The three-dimensional model is used to generate the customized resorbable three-dimensional scaffold and resorbable connectors for the customized resorbable three-dimensional scaffold.

20 Claims, 10 Drawing Sheets

(56) References Cited

U.S. PATENT DOCUMENTS

| | | |
|---|---|---|
| 10,835,640 B2 | 11/2020 | Stiefel et al. |
| 2004/0258729 A1 | 12/2004 | Czernuszka et al. |
| 2012/0244498 A1 | 9/2012 | Hall |
| 2013/0209961 A1 | 8/2013 | Rubbert et al. |
| 2016/0374784 A1* | 12/2016 | Joshi .................... A61C 9/0053 433/214 |
| 2020/0167514 A1* | 5/2020 | Greyf ........................ A61F 2/28 |

* cited by examiner

CUSTOMIZED THREE-DIMENSIONAL SCAFFOLD FOR ORAL AND MAXILLOFACIAL BONE GRAFTING

BACKGROUND

Technical Field

Embodiments of the disclosed subject matter generally relate to systems and methods for creating and using a three-dimensional scaffold for oral and maxillofacial bone grafting that is customized for the patient and includes resorbable material.

Discussion of the Background

Compared to many other medical fields, the field of dental surgery employs relatively rudimentary techniques for bone repair. A dental surgeon typically obtains a two- or three-dimensional image of the area for the bone repair and then orders premanufactured scaffolds (typically constituted as membranes or mesh), which are manufactured with fixed sizes and are not customized for the patient. The dental surgeon must first make extensive customizations to the shape of the premanufactured scaffold using, for example, a milling or grinding tool to conform to the area of the bone repair. Due to form instabilities and material thickness, the customized scaffolds may not fit well, which can affect the proper tissue closure after the surgery, which in turn requires regrafting any exposed areas and any failures.

The dental surgeon then opens the tissue in the area of the bone repair, inserts the scaffold and the bone graft, and then closes the tissue in the area of bone repair. The placement of the bone by the dental surgeon is typically based purely on the judgment of the dental surgeon and errors in judgement can require regrafting. Regrafting necessitates opening the tissue in the area of bone repair again, which involves an additional visit by the patient, as well as increases risks of infection.

Additionally, despite the scaffolds being premanufactured in fixed sizes, the overall costs for surgically inserting these scaffolds can be quite high, which can be problematic for patients since, unlike health insurance, dental insurance typically requires the patient to be responsible for a large portion of the costs of the dental services. These costs involve increased surgical time to customize the premanufactured scaffold to adapt the scaffold to the patient's bone for surgery. Further, because the dental surgeon uses subtractive methods to customize the scaffold, there is typically a large amount of the sterilized premanufactured scaffold that is grinded or milled off of the premanufactured scaffold, which is essentially wasted.

Thus, there is a need for a method and system to produce a three-dimensional scaffold for oral and maxillofacial bone grafting that is customized for the patient, as well as is available at a lower cost compared to obtaining a premanufactured scaffold.

SUMMARY

According to embodiments, there is a method for making a customized and resorbable three-dimensional scaffold for oral and maxillofacial bone grafting, the method. Two different sets of three-dimensional information obtained from a patient are obtained, wherein a first set of the two different sets includes three-dimensional bone information and a second set of the two different sets includes three-dimensional teeth and tissue information. The first and second sets of three-dimensional information are merged to form merged three-dimensional information. Using the merged three-dimensional information, a three-dimensional shape of the bone to be regenerated is generated. Using the merged three-dimensional information and based on esthetic, phonetic, and functional parameters, a three-dimensional position of missing tooth/teeth is generated. Using the merged three-dimensional information, the three-dimensional position of the missing tooth/teeth, and the three-dimensional shape of the bone to be regenerated, a three-dimensional model of the customized resorbable three-dimensional scaffold for oral and maxillofacial bone grafting is generated. Using the three-dimensional model of the customized three-dimensional scaffold, the customized resorbable three-dimensional scaffold and resorbable connectors for the customized resorbable three-dimensional scaffold are generated.

According to embodiments, there is a system for making a customized and resorbable three-dimensional scaffold for oral and maxillofacial bone grafting. The system includes a computer comprising a non-transitory memory and a processor coupled to the non-transitory memory. The processor is configured to obtain two different sets of three-dimensional information obtained from a patient, wherein a first set of the two different sets includes three-dimensional bone information and a second set of the two different sets includes three-dimensional teeth and tissue information; merge the first and second sets of three-dimensional information to form merged three-dimensional information; generate, using the merged three-dimensional information, a three-dimensional shape of the bone to be regenerated; generate, using the merged three-dimensional information and based on esthetic, phonetic, and functional parameters, a three-dimensional position of missing tooth/teeth; generate, using the merged three-dimensional information, the three-dimensional position of the missing tooth/teeth, and the three-dimensional shape of the bone to be regenerated, a three-dimensional model of the customized resorbable three-dimensional scaffold for oral and maxillofacial bone grafting. The system also includes a computer numerical control machine or a three-dimensional printer that generates, using the three-dimensional model of the customized three-dimensional scaffold, the customized resorbable three-dimensional scaffold and resorbable connectors for the customized resorbable three-dimensional scaffold.

According to embodiments there is a non-transitory computer readable medium storing a computer program, which when executed by a processor, causes the processor to: obtain two different sets of three-dimensional information obtained from a patient, wherein a first set of the two different sets includes three-dimensional bone information and a second set of the two different sets includes three-dimensional teeth and tissue information; merge the first and second sets of three-dimensional information to form merged three-dimensional information; generate, using the merged three-dimensional information, a three-dimensional shape of the bone to be regenerated; generate, using the merged three-dimensional information and based on esthetic, phonetic, and functional parameters, a three-dimensional position of missing tooth/teeth; generate, using the merged three-dimensional information, the three-dimensional position of the missing tooth/teeth, and the three-dimensional shape of the bone to be regenerated, a three-dimensional model of the customized resorbable three-dimensional scaffold for oral and maxillofacial bone grafting; and output the three-dimensional model of the customized three-dimensional scaffold to a computer numerical control machine or a three-dimensional printer, wherein the computer numerical control machine or the three-dimensional printer generates, using the three-dimensional model of the customized three-dimensional scaffold, the customized resorbable three-dimensional scaffold and resorbable connectors for the customized resorbable three-dimensional scaffold.

BRIEF DESCRIPTION OF THE DRAWINGS

The accompanying drawings, which are incorporated in and constitute a part of the specification, illustrate one or more embodiments and, together with the description, explain these embodiments. In the drawings.

DETAILED DESCRIPTION

The following description of the exemplary embodiments refers to the accompanying drawings. The same reference numbers in different drawings identify the same or similar elements. The following detailed description does not limit the invention. Instead, the scope of the invention is defined by the appended claims. The following embodiments are discussed, for simplicity, with regard to the terminology and structure of oral and maxillofacial bone grafting.

Reference throughout the specification to "one embodiment" or "an embodiment" means that a particular feature, structure or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

Figure 1:
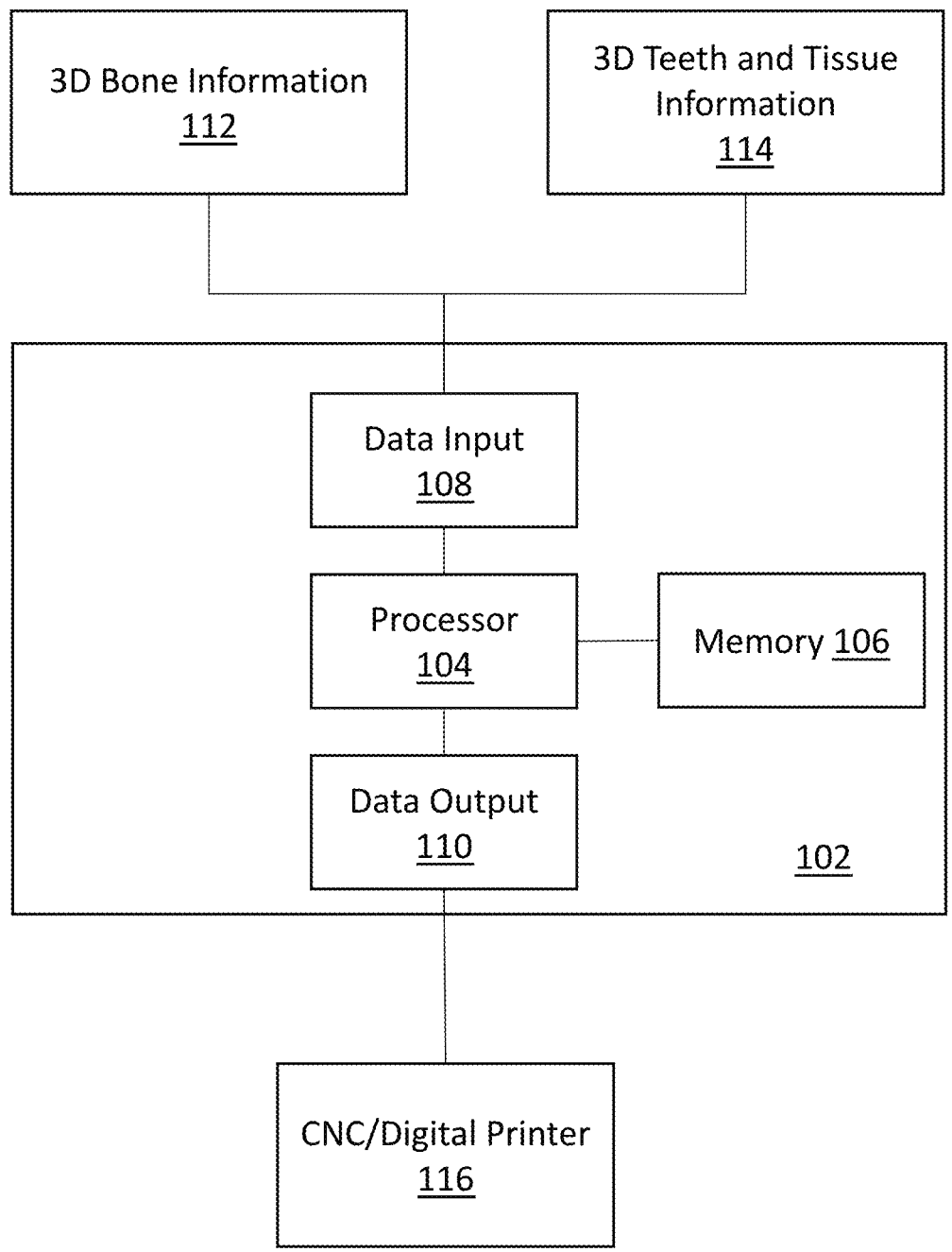
FIG. 1 is a block diagram of a system for making a customized and resorbable three-dimensional scaffold for oral and maxillofacial bone grafting according to embodiments.

FIG. 1 is a block diagram of a system for making a customized and resorbable three-dimensional scaffold for oral and maxillofacial bone grafting according to embodiments. The system includes a computer 102, which has a processor 104. Computer 102 can be any type of computer, including a desktop, laptop, or handheld computer, a server, and the like. Processor 104 can be any type of processor, including a microprocessor, field programmable gate array (FPGA), application specific integrated circuit (ASIC), etc.

Processor 104 is coupled to a memory 106, a data input 108, and a data output 110. Memory 106 can be any type of non-transitory computer-readable storage medium, including read-only memory (ROM), random access memory (RAM), a hard drive, a solid state drive, etc. Memory 106 stores a computer program to execute the method illustrated in the flowchart of FIG. 2, as well as any other data necessary to perform the method, including the three-dimensional bone information and three-dimensional teeth and tissue information, as will be described in more detail below.

The processor 104 is coupled, via data input 108, to a source of three-dimensional (3D) bone information of the bone being repaired 112 and a source of three-dimensional teeth and tissue information 114. The processor 104 is also coupled, via data output 110, to a computer numerical control machine and/or a digital printer 116. The data input 108 and data output 110 can be ports for attaching cables to the computer, a memory reader (e.g., a CD, DVD, Blu-ray reader, a solid state memory reader, etc.), a wireless connection (e.g., a Wi-Fi, Bluetooth, cellular connection, etc.), or any other component for inputting information to and outputting information from the computer 102 consistent with this disclosure. For ease of illustration, and not limitation, the data input 108 and data output 110 are illustrated as separate components, these can be integrated into a single component. Further, the three-dimensional bone formation source 112 and the three-dimensional teeth and tissue information source 114 can be coupled to the computer 102 using different data inputs that can be the same or different types of data inputs.

Figure 2A:
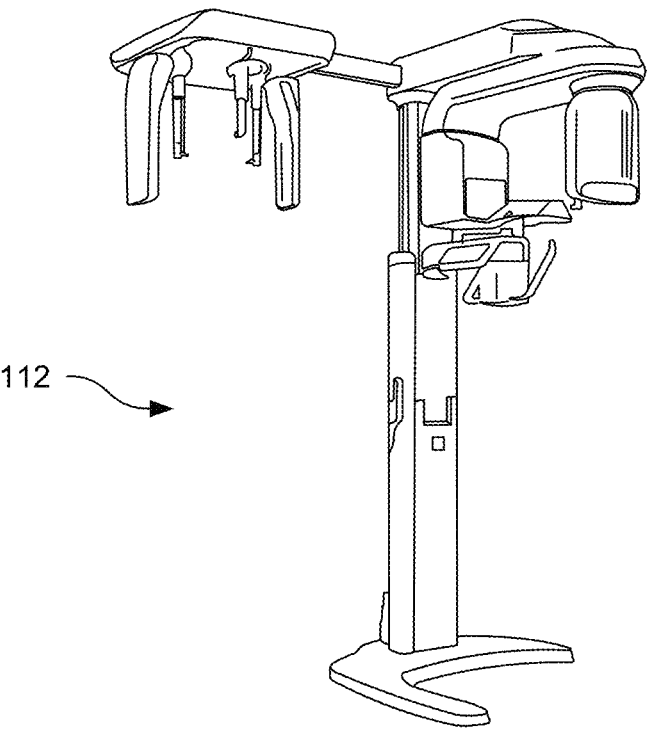
FIG. 2A illustrates a three-dimensional computer tomography (CT) scanner according to embodiments.
Figure 2B:
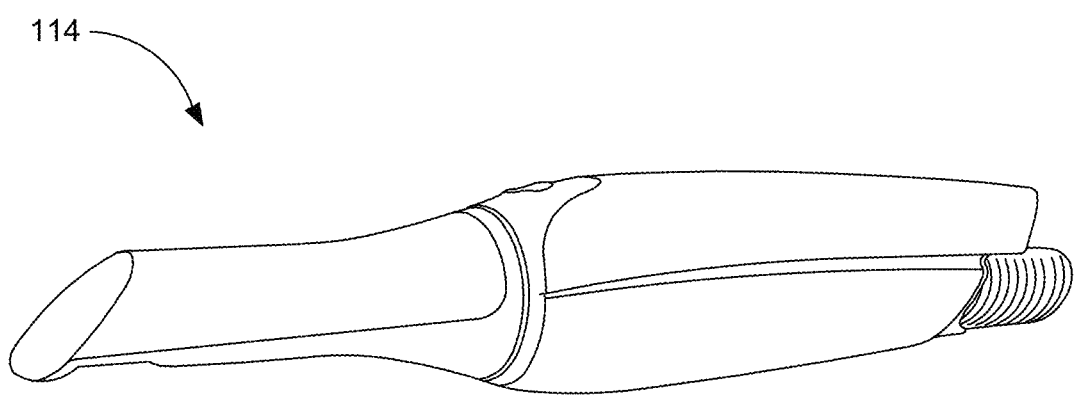
FIG. 2B illustrates a three-dimensional surface scanner according to embodiments.

The source of the three-dimensional bone information 112 can be, for example, a three-dimensional computer tomography (CT) scanner or any other imaging device capable of obtaining three-dimensional information about bones that are repairable during oral and/or maxillofacial surgery. An exemplary three-dimensional CT scanner is illustrated in FIG. 2A. Such scanners typically output the three-dimensional information in a DICOM formatted file. The source of three-dimensional teeth and tissue information 114 can be, for example, a surface scanner or any other type of imaging device that can obtain a three-dimensional image of teeth and surrounding tissue for use during oral and/or maxillofacial surgery. An exemplary three-dimensional surface scanner is the TRIOS 4 manufactured by 3shape, and illustrated in FIG. 2B. Such scanners typically output the three-dimensional information in an STL formatted file.

The computer numerical control machine and/or digital printer 116 can be any type of computer numerical control machine or digital printer that can print the disclosed scaffold using resorbable material. In one embodiment, the resorbable material is magnesium. Specifically, the resorbable material can comprise magnesium (i.e., include magnesium as well as other material) or can consist essentially of magnesium (i.e., the at least 99% of the material is magnesium and the remainder of the material is impurities that are necessarily introduced while forming the scaffold using a computer numerical control machine or digital printer.

For ease of illustration, and not limitation, only some components of the computer 102 are illustrated. It should be recognized, however, that the computer 102 can have additional components, such as input devices (e.g., keyboard, trackpad, trackball, mouse, document scanner, etc.), output devices (e.g., a display or monitor, a printer, etc.), additional processors, additional memories, additional data inputs, and additional data outputs, etc.

Figure 3:
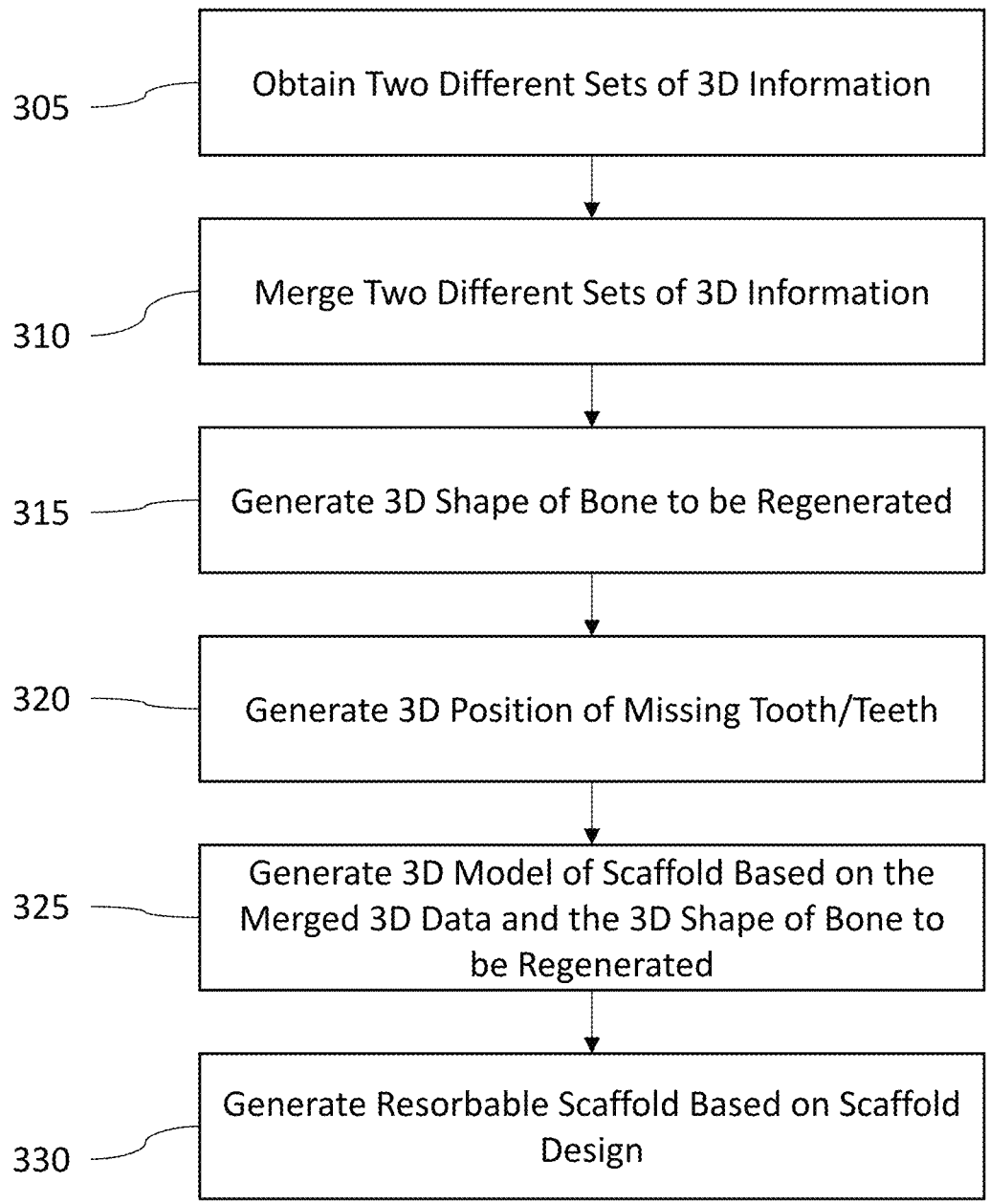
FIG. 3 is a flow diagram of a method for making a customized and resorbable three-dimensional scaffold for oral and maxillofacial bone grafting according to embodiments.
Figure 4A:
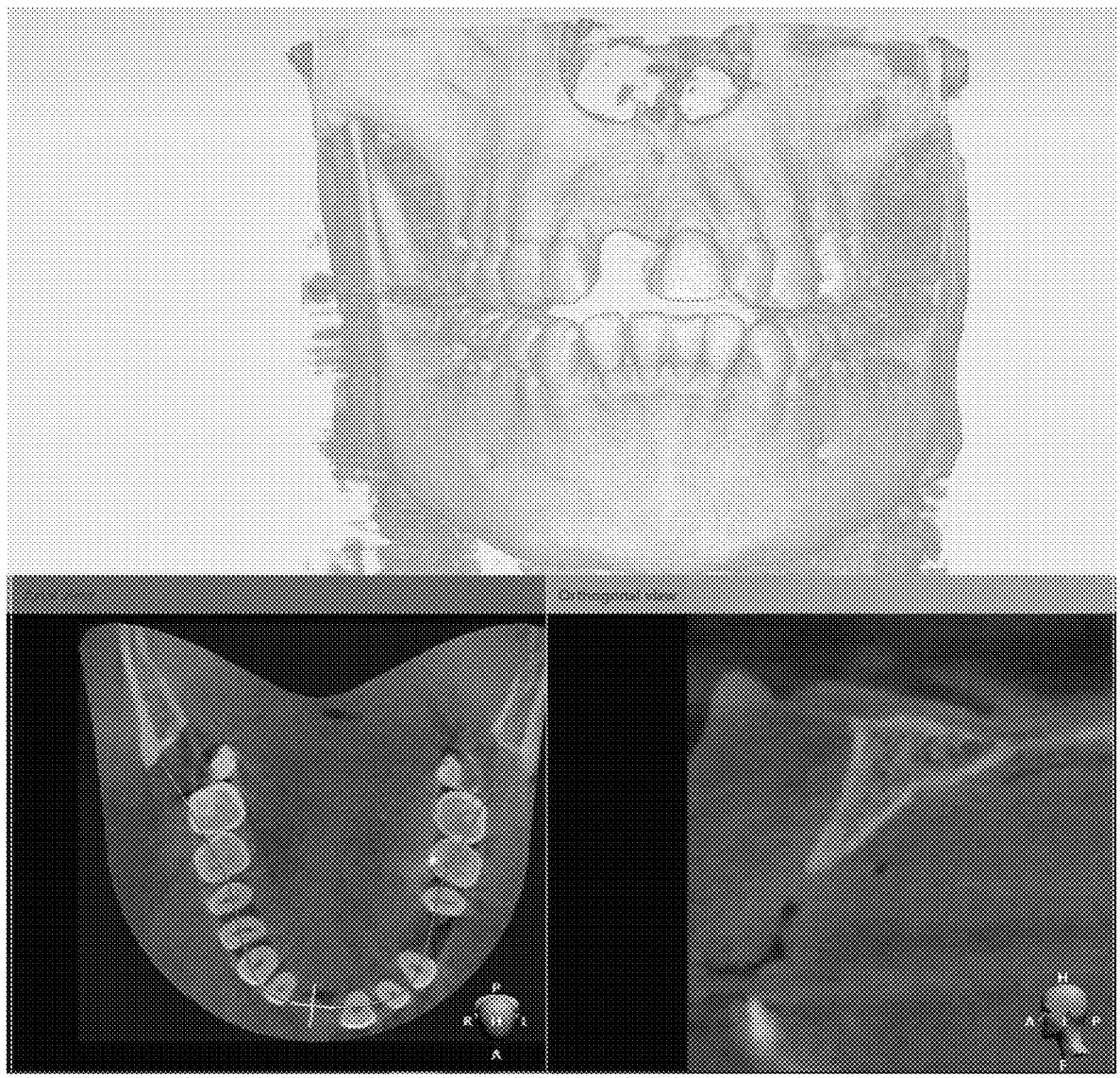
FIG. 4A illustrates captured three-dimensional bone information according to embodiments.
Figure 4B:
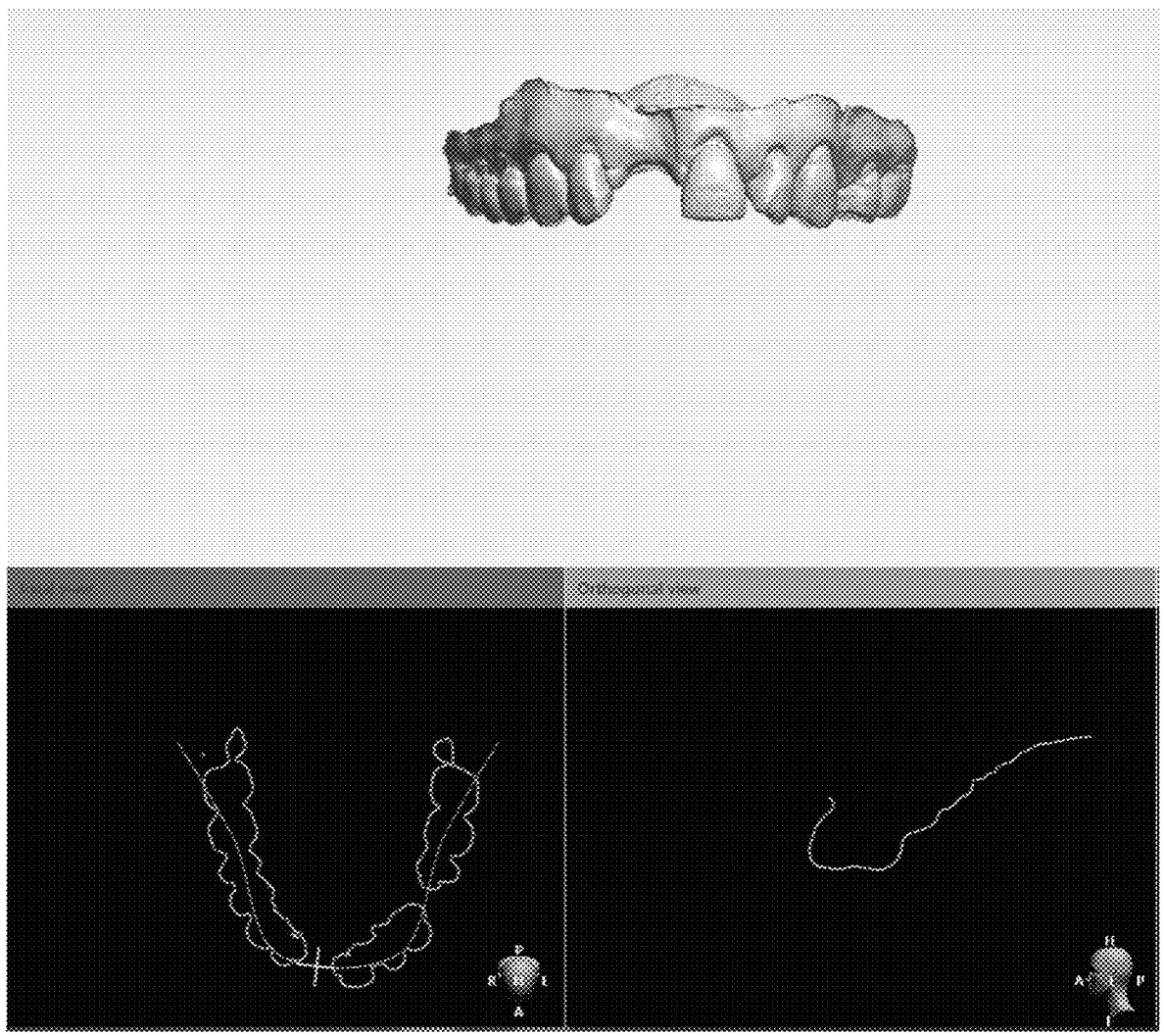
FIG. 4B illustrates captured three-dimensional teeth and tissue information according to embodiments.
Figure 4C:
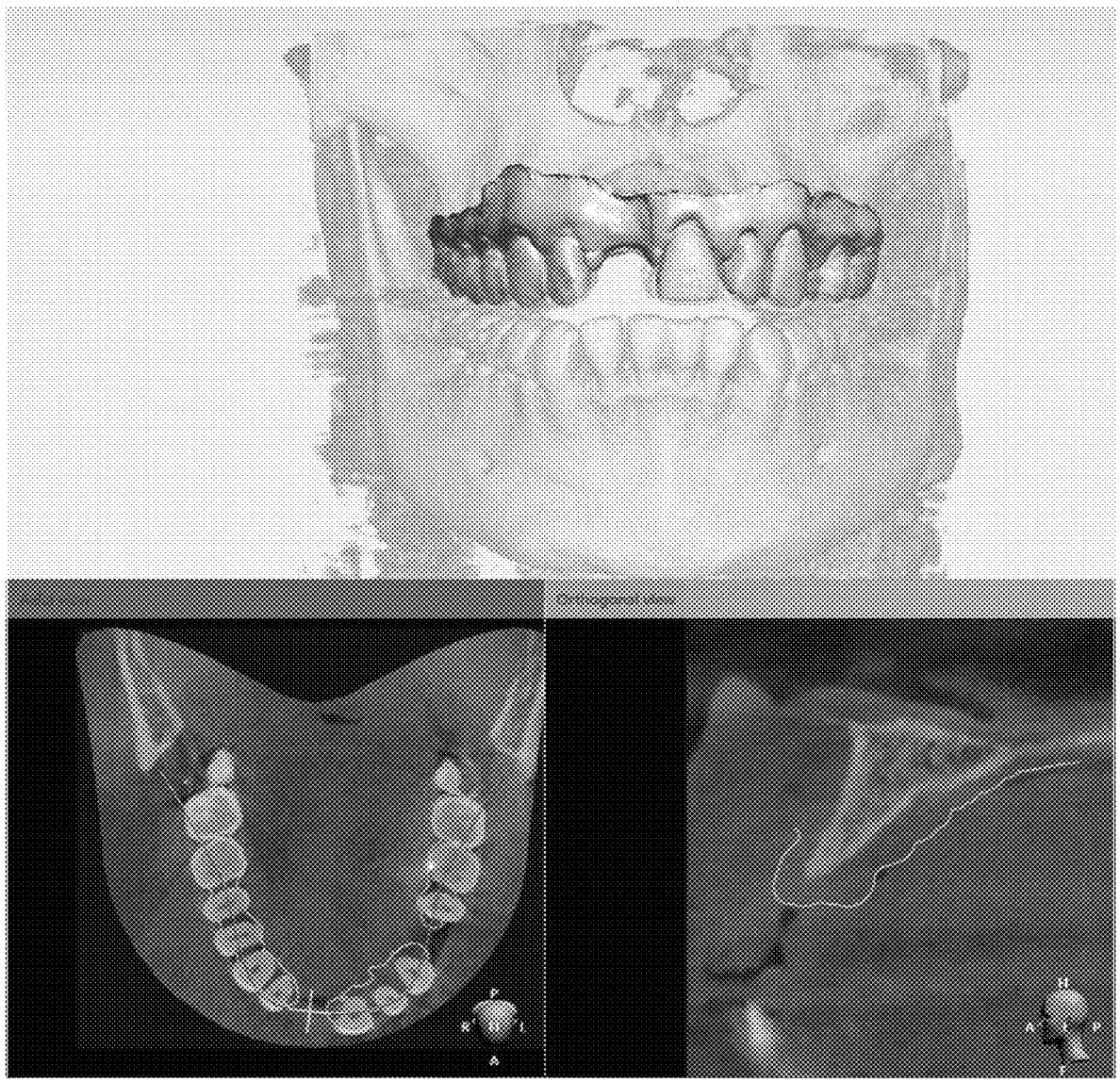
FIG. 4C illustrates merged three-dimensional bone information and three-dimensional teeth and tissue information.

A method for making a customized and resorbable three-dimensional scaffold for oral and maxillofacial bone grafting will now be described in connection with the block diagram of FIG. 1, the flowchart of FIG. 3, and the example images of FIGS. 4A-4C. Initially, the computer 105 obtains two different sets of three-dimensional information from a patient (step 305). A first set of the two different sets includes three-dimensional bone information and a second set of the two different sets includes three-dimensional teeth and tissue information. FIG. 4A illustrates an exemplary set of three-dimensional bone information, the top pane showing a three-dimensional view, the lower left pane showing an axial view, and the lower right pane showing an orthogonal view. FIG. 4B illustrates an exemplary set of three-dimensional teeth and tissue information, the top pane showing a three-dimensional view, the lower left pane showing an axial view, and the lower right pane showing an orthogonal view. As discussed above, the computer 105 obtains, via data input 108, the first set of data from three-dimensional bone information source 112 and the second set of data from the three-dimensional teeth and tissue information source 114.

The computer 105 then merges the first and second sets of three-dimensional information to form merged three-dimensional information (step 310). The merging can be performed using a conventional computer-aided design (CAD) program. An example of the merged three-dimensional information from the three-dimensional bone information (FIG. 4A) and the three-dimensional teeth and tissue information (FIG. 4B) is illustrated in FIG. 4C, the top pane illustrating the merged three-dimensional data, the lower left pane showing the merged data in an axial view, and the lower right pane showing the merged data in an orthogonal view. Using the merged three-dimensional information, the computer 105 generates a three-dimensional shape of the tissue and bone to be regenerated (step 315). This can be performed using, for example, a CAD program.

The computer 105 also generates a three-dimensional position of the missing tooth/teeth using the merged three-dimensional information and based on esthetic, phonetic, and functional parameters (step 320). This can be accomplished, for example, by an operator viewing the merged three-dimensional information using a CAD program and utilizing the operator's experience to correct deficiencies in the mouth, such as missing teeth, tissue, and bone. Those skilled in the art will recognize that dental esthetic involves a correlation of dental and facial midline, upper lip position and curvature, relationship of the maxillary anterior incisal curve with the lower lip, number of teeth displayed in a smile, distance between upper and lower anterior teeth and lips, and overall balancing of teeth shape and teeth position within the upper and lower arch. Dental function refers to effective breaking down (masticating) of food. Dental phonetics relates to proper pronunciation of sounds. Both dental function and phonetics are affected by the teeth, tissue, and bone shapes and positions. It should be recognized that the position of the tooth/teeth determines the position of the scaffold, replacement tooth/teeth, and dental implant, and accordingly the bone volume to be regenerated.

Figure 4D:
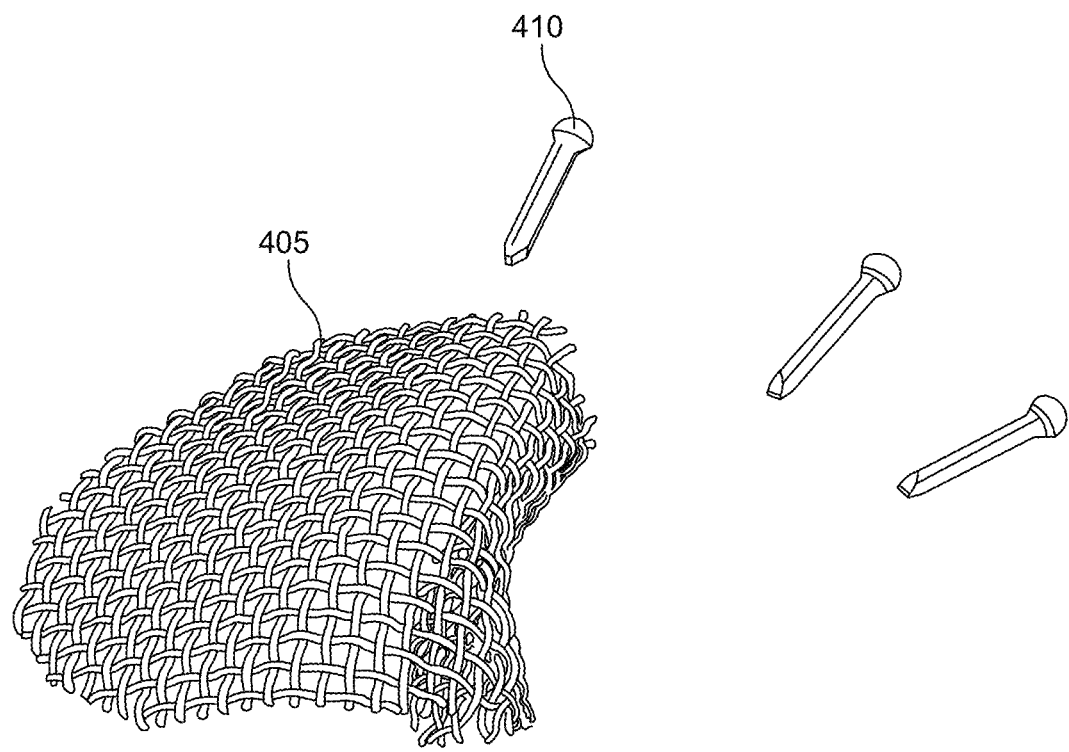
FIG. 4D illustrates a customized resorbable three-dimensional scaffold and resorbable connectors according to embodiments.

The computer 105, via a CAD program, uses the merged three-dimensional information, the three-dimensional position of the missing tooth/teeth, and the three-dimensional shape of the bone to be regenerated to generate a three-dimensional model of the customized resorbable three-dimensional scaffold for oral and maxillofacial bone grafting (step 325). The computer 105 provides the three-dimensional model of the customized resorbable three-dimensional scaffold to the computer numerical controlled machine and/or digital printer, which then generates, using the three-dimensional model of the customized three-dimensional scaffold, the customized resorbable three-dimensional scaffold and resorbable connectors for the customized resorbable three-dimensional scaffold (step 330). Specifically, a computer numerical controlled machine can generate the customized three-dimensional scaffold from a material using a subtractive technique that removes portions of the material to achieve the desired shape of the customized three-dimensional scaffold and the digital printer uses an additive technique that generates the customized three-dimensional scaffold by printing using an ink having a resorbable material, such as a magnesium-based ink. FIG. 4D illustrates an exemplary customized resorbable three-dimensional scaffold 405 and resorbable connectors 410 (only one of which is labeled). As illustrated, the customized resorbable three-dimensional scaffold 405 has a non-regular shape that is specifically customized for a particular patient.

Figure 5:
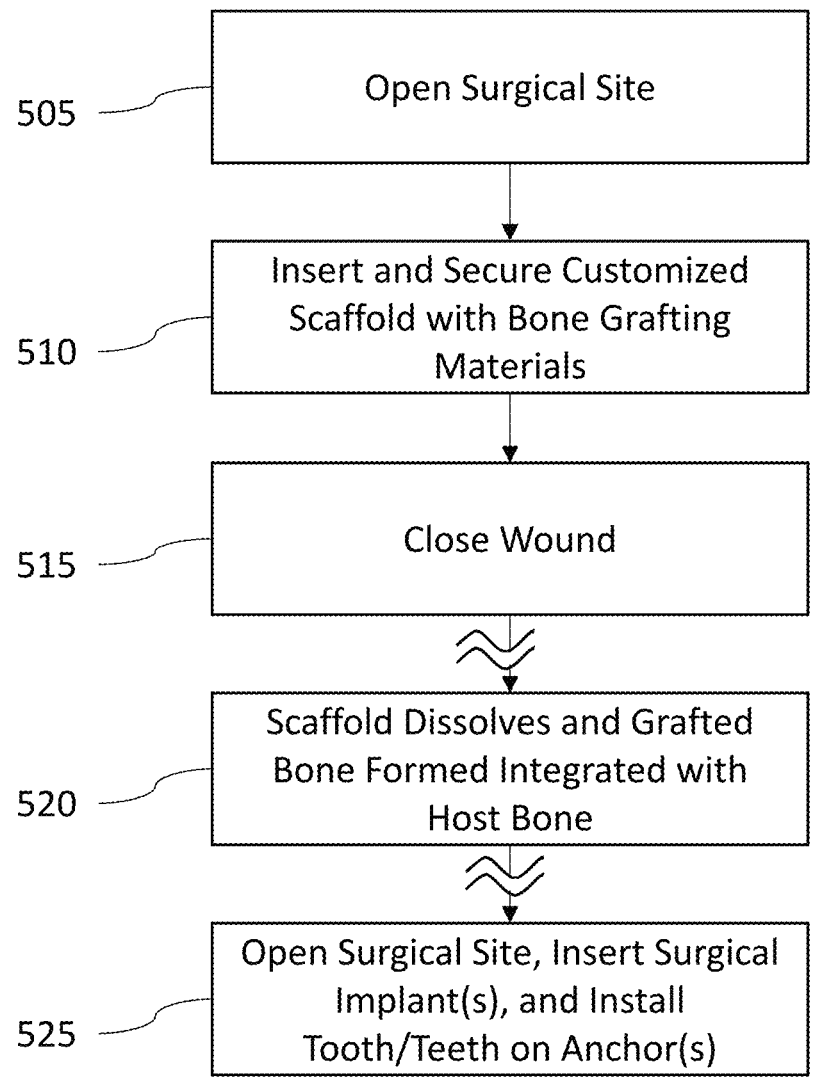
FIG. 5 is a flow diagram of a method for inserting a customized and resorbable three-dimensional scaffold for oral and maxillofacial bone grafting in a patient.
Figure 6A:
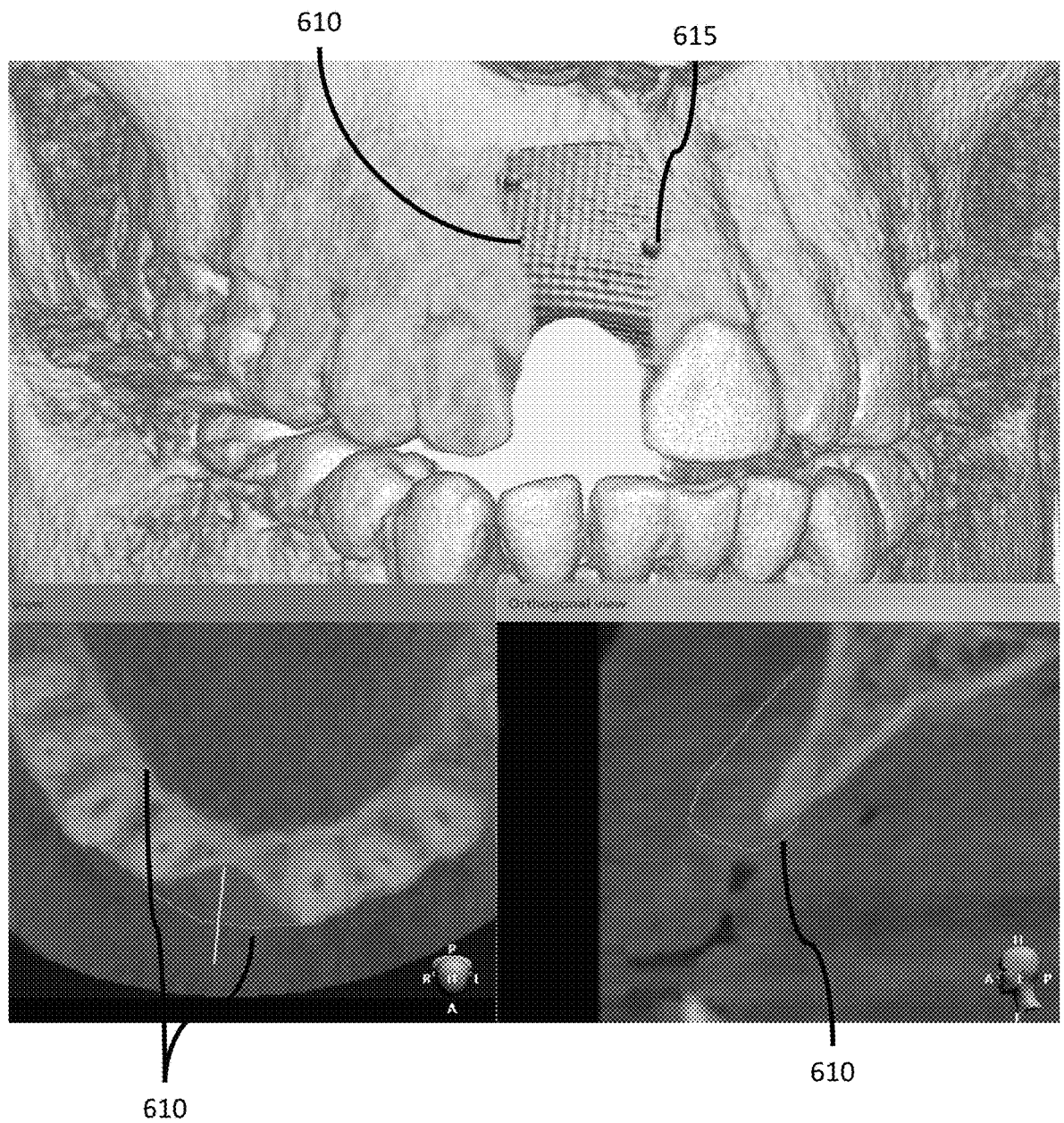
FIG. 6A illustrates a customized resorbable three-dimensional scaffold and resorbable connectors inserted into a patients mouth according to embodiments.

A method for oral or maxillofacial bone grafting can involve the method described above in connection with FIG. 3 to make the customized and resorbable three-dimensional scaffold, and the method of FIG. 5 to surgically insert the customized and resorbable three-dimensional scaffold. Specifically, a tissue area around the damaged bone is opened (step 505) and the customized and resorbable three-dimensional scaffold is then surgically inserted and secured to the damaged bone along with bone grafting materials (step 510). Those skilled in the art would understand the types of bone grafting materials that are appropriate for oral and maxillofacial bone grafting. FIG. 6A illustrates an exemplary customized and resorbable three-dimensional scaffold 610 and pins 615 (only one of which is labeled), with the top pane illustrating a three-dimensional view, the lower left pane illustrating an axial view, and the lower right pane illustrating an orthogonal view. As will be appreciated from the top pane of FIG. 6A, the resorbable three-dimensional scaffold has been customized into a non-uniform shape for the particular patient. Note in particular the difference shapes of the upper left and right sides of the customized and resorbable three-dimensional scaffold, which are differently shaped to accommodate the existing bone structure in the patient's mouth.

Figure 6B:
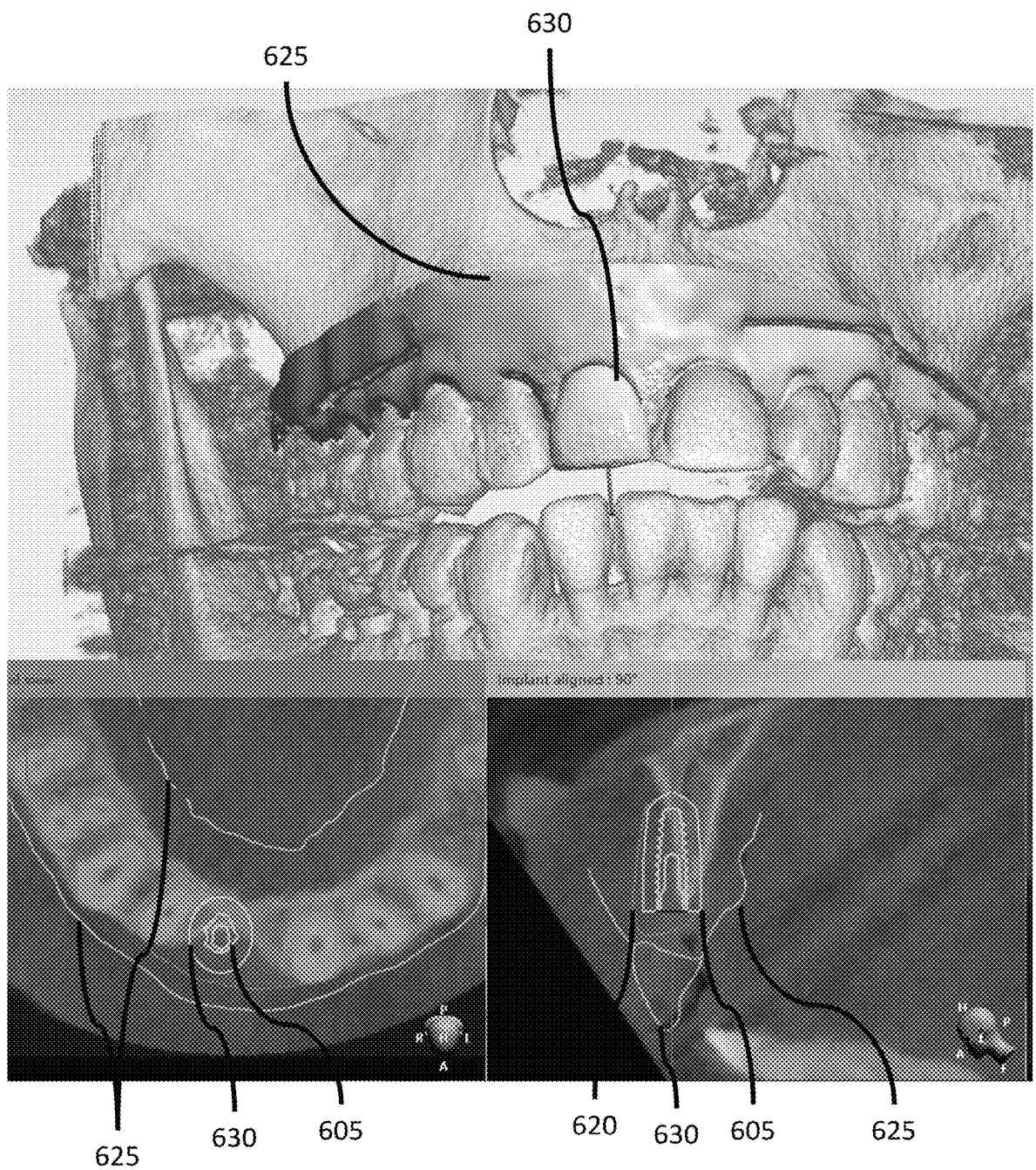
FIG. 6B illustrates a patient's mouth after inserting a replacement tooth according to embodiments.

The wound formed by opening the tissue area around the damaged bone is then closed (step 515). Over a period of time, which depends upon the type of resorbable material employed, the scaffold dissolves and the grafted bone is formed integrated with the host bone, i.e., the damaged bone (step 520). Any time after the grafted bone is integrated with the host bone, the surgical site can be opened again, a dental implant for the replacement tooth or dental implants for replacement teeth can be inserted into the regenerated bone, and the replacement tooth or teeth can be installed on the inserted dental implant(s) (step 525). An example of this is illustrated in FIG. 6B, where the top pane is a three-dimensional view, the lower left pane is an axial view, and the lower right pane is an implant-aligned 90° view. As illustrated, the bone 620 and tissue 625 have grown over the dental implant 605 and the tooth 630 is secured to the dental implant 605.

Because, as described above, the three-dimensional scaffold is designed based on both the three-dimensional bone information of the patient and the three-dimensional teeth and tissue information of the patient, the three-dimensional scaffold has been optimized for the actual conditions of the patient, which contrasts with the conventional way of using premanufactured scaffolds. Further, the use of the three-dimensional teeth and tissue information of the patient provides for the optimized design of the three-dimensional scaffold that accounts for aspects other than the damaged bone. Thus, as discussed above, conventional scaffolds that are incorrectly placed can result in pressure placed on the scaffold by the tissue, obtaining and using the three-dimensional teeth and tissue information allows the scaffold to avoid this issue because it is optimized for the teeth and tissue in the area of the damaged bone.

It should be recognized that the particular illustrations in FIGS. 4A-4D, 6A, and 6B are merely exemplary and are presented to assist in the understanding of the invention, and should not be interpreted as limiting in any way. Indeed, depending upon which tooth or teeth are being replaced, as well as the particular structure of the patients mouth, the customized resorbable three-dimensional scaffold can be differently shaped so that it is customized for the particular patient.

The disclosed embodiments provide systems and methods for producing and employing customized three-dimensional scaffolds for oral and maxillofacial bone grating. It should be understood that this description is not intended to limit the invention. On the contrary, the exemplary embodiments are intended to cover alternatives, modifications and equivalents, which are included in the spirit and scope of the invention as defined by the appended claims. Further, in the detailed description of the exemplary embodiments, numerous specific details are set forth in order to provide a comprehensive understanding of the claimed invention. However, one skilled in the art would understand that various embodiments may be practiced without such specific details.

Although the features and elements of the present exemplary embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

What is claimed is:

1. A method for making a customized and resorbable three-dimensional scaffold for oral and maxillofacial bone grafting, the method comprising:
   obtaining two different sets of three-dimensional information obtained from a patient, wherein a first set of the two different sets includes three-dimensional bone information and a second set of the two different sets includes three-dimensional teeth and tissue information;
   merging the first and second sets of three-dimensional information to form merged three-dimensional information;
   generating, using the merged three-dimensional information, a three-dimensional shape of the bone to be regenerated;
   generating, using the merged three-dimensional information and based on esthetic, phonetic, and functional parameters, a three-dimensional position of missing tooth/teeth;
   generating, using the merged three-dimensional information, the three-dimensional position of the missing tooth/teeth, and the three-dimensional shape of the bone to be regenerated, a three-dimensional model of the customized resorbable three-dimensional scaffold for oral and maxillofacial bone grafting; and
   generating, using the three-dimensional model of the customized three-dimensional scaffold, the customized resorbable three-dimensional scaffold and resorbable connectors for the customized resorbable three-dimensional scaffold.

2. The method of claim 1, wherein the first set of information is obtained using a computerized tomography scanner.

3. The method of claim 1, wherein the second set of information is obtained using a surface scanner.

4. The method of claim 1, wherein the customized resorbable three-dimensional scaffold and the resorbable connectors are generated using computer numerical control machine.

5. The method of claim 1, wherein the customized resorbable three-dimensional scaffold and the resorbable connectors are generated using a three-dimensional printer.

6. The method of claim 1, wherein the customized resorbable three-dimensional scaffold and the resorbable connectors comprise magnesium.

7. The method of claim 1, wherein the customized resorbable three-dimensional scaffold and the resorbable connectors consist essentially of magnesium.

8. The method of claim 1, wherein the first and second sets of three-dimensional information are merged using a computer-aided design program.

9. A system for making a customized and resorbable three-dimensional scaffold for oral and maxillofacial bone grafting, the system comprising:
   a computer comprising a non-transitory memory and a processor coupled to the non-transitory memory, wherein the processor is configured to
      obtain two different sets of three-dimensional information obtained from a patient, wherein a first set of the two different sets includes three-dimensional bone information and a second set of the two different sets includes three-dimensional teeth and tissue information;
      merge the first and second sets of three-dimensional information to form merged three-dimensional information;
      generate, using the merged three-dimensional information, a three-dimensional shape of the bone to be regenerated;
      generate, using the merged three-dimensional information and based on esthetic, phonetic, and functional parameters, a three-dimensional position of missing tooth/teeth;
      generate, using the merged three-dimensional information, the three-dimensional position of the missing tooth/teeth, and the three-dimensional shape of the bone to be regenerated, a three-dimensional model of the customized resorbable three-dimensional scaffold for oral and maxillofacial bone grafting; and
   a computer numerical control machine or a three-dimensional printer that generates, using the three-dimensional model of the customized three-dimensional scaffold, the customized resorbable three-dimensional scaffold and resorbable connectors for the customized resorbable three-dimensional scaffold.

10. The system of claim 9, further comprising:
a computerized tomography scanner that generates the first set of information is obtained.

11. The system of claim 9, further comprising:
a surface scanner that generates the second set of information.

12. The system of claim 9, wherein the customized resorbable three-dimensional scaffold and the resorbable connectors comprise magnesium.

13. The system of claim 9, wherein the customized resorbable three-dimensional scaffold and the resorbable connectors consist essentially of magnesium.

14. The system of claim 9, wherein the processor executes a computer-aided design program to merge the first and second sets of three-dimensional information.

15. A non-transitory computer readable medium storing a computer program, which when executed by a processor, causes the processor to:
obtain two different sets of three-dimensional information obtained from a patient, wherein a first set of the two different sets includes three-dimensional bone information and a second set of the two different sets includes three-dimensional teeth and tissue information;
merge the first and second sets of three-dimensional information to form merged three-dimensional information;
generate, using the merged three-dimensional information, a three-dimensional shape of the bone to be regenerated;
generate, using the merged three-dimensional information and based on esthetic, phonetic, and functional parameters, a three-dimensional position of missing tooth/teeth;
generate, using the merged three-dimensional information, the three-dimensional position of the missing tooth/teeth, and the three-dimensional shape of the bone to be regenerated, a three-dimensional model of the customized resorbable three-dimensional scaffold for oral and maxillofacial bone grafting; and
output the three-dimensional model of the customized three-dimensional scaffold to a computer numerical control machine or a three-dimensional printer, wherein the computer numerical control machine or the three-dimensional printer generates, using the three-dimensional model of the customized three-dimensional scaffold, the customized resorbable three-dimensional scaffold and resorbable connectors for the customized resorbable three-dimensional scaffold.

16. The non-transitory computer readable medium of claim 15, wherein the processor obtains the first set of information from a computerized tomography scanner.

17. The non-transitory computer readable medium of claim 15, wherein the processor obtains the second set of information from a surface scanner.

18. The non-transitory computer readable medium of claim 15, wherein the customized resorbable three-dimensional scaffold and the resorbable connectors comprise magnesium.

19. The non-transitory computer readable medium of claim 15, wherein the customized resorbable three-dimensional scaffold and the resorbable connectors consist essentially of magnesium.

20. The non-transitory computer readable medium of claim 15, wherein the processor uses a computer-aided design program to merge the first and second sets of three-dimensional information.

* * * * *